United States Patent [19]

Ram

[11] Patent Number: 5,593,304
[45] Date of Patent: Jan. 14, 1997

[54] DENTAL APPARATUS INCLUDING MULTIPLE-USE ELECTRICALLY-OSCILLATED HANDPIECE

[76] Inventor: Zeev Ram, 9 Yaacov Street, 76262 Rehovot, Israel

[21] Appl. No.: 491,447

[22] Filed: Jun. 16, 1995

[51] Int. Cl.⁶ .................. A61C 1/10; A61C 1/07; A61C 17/06
[52] U.S. Cl. .................. 433/82; 433/84; 433/92; 433/118
[58] Field of Search .................. 433/29, 80, 82, 433/84, 85, 92, 114, 118, 119, 147, 215

[56] References Cited

U.S. PATENT DOCUMENTS

| | | | |
|---|---|---|---|
| 3,133,351 | 5/1964 | Von Seggern | 433/119 |
| 3,255,079 | 6/1966 | Schoeder et al. | 424/642 |
| 3,335,443 | 8/1967 | Parisi et al. | 433/119 |
| 3,636,947 | 1/1972 | Balamuth | 601/162 |
| 3,718,973 | 3/1973 | Slater et al. | 433/80 X |
| 3,783,515 | 1/1974 | Auphan et al. | 433/82 |
| 3,828,770 | 8/1974 | Kuris et al. | 601/142 |
| 4,302,185 | 11/1981 | Hall | 433/84 X |
| 4,333,197 | 6/1982 | Kuris | 433/119 |
| 4,425,094 | 1/1984 | Tateosian et al. | 433/228 |
| 4,489,080 | 12/1984 | Lomen | 424/260 |
| 4,505,676 | 3/1985 | Gonser | 433/119 |
| 4,576,190 | 3/1986 | Youssef | 132/322 |
| 4,735,200 | 4/1988 | Westerman | 15/22.2 |
| 4,903,688 | 2/1990 | Bibby et al. | 433/88 |
| 4,917,603 | 4/1990 | Haack | 433/29 |
| 4,991,249 | 2/1991 | Suroff | 433/127 |
| 5,029,358 | 7/1991 | Zimmerman | 15/167.1 |
| 5,044,952 | 9/1991 | Castellini | 433/84 |
| 5,055,043 | 10/1991 | Weiss | 433/86 |
| 5,147,203 | 9/1992 | Seidenberg | 433/85 X |
| 5,393,229 | 2/1995 | Ram | 433/118 |

Primary Examiner—Robert P. Swiatek
Assistant Examiner—Elizabeth Shaw
Attorney, Agent, or Firm—Ladas & Parry

[57] ABSTRACT

Dental apparatus includes a handpiece graspable at one end by a user, and a head at the opposite end of the handpiece including a single nozzle, or a pair of nozzles, connectible to a source of a liquid, a gas, and/or powder. An electrical oscillating drive within the handpiece oscillates the head; and a manual fluid selector device manually selects the liquid, gas, and/or powder for conduction to the single nozzle or to the pair of nozzles.

20 Claims, 2 Drawing Sheets

DENTAL APPARATUS INCLUDING MULTIPLE-USE ELECTRICALLY-OSCILLATED HANDPIECE

FIELD AND BACKGROUND OF THE INVENTION

The present invention relates to dental apparatus, and particularly to such apparatus which includes a multiple-use electrically-oscillated handpiece.

Various types of dental implements are known including a handpiece having an oscillating drive. One type includes a metal tip which is used with a water spray for dislodging calculus and stain; an example of this type is the "Dentsply/Cavitron" (Reg. TMs), Model 700-11, ultrasonic dental unit supplied by Dentsply International Inc., of York, Pa. Another type, described in my prior U.S. Pat. No. 5,393,229, includes a head releasably attaching a wooden toothpick, and a spray nozzle for discharging a liquid spray in the region of the toothpick when used. The latter implement has been found particularly effective not only for cleaning the teeth and the spaces between the teeth, but also the spaces between the teeth and the gums (the sulcus).

The conventional dental unit as commonly found in dental offices includes an air inlet to be coupled to a source of pressurized air, a water inlet to be coupled to a source of pressurized water (usually the water tap), and outlet couplings for coupling various dental appliances to be used for treating the patient. U.S. Pat. No. 5,055,043, of which I am a joint inventor, describes dental apparatus which also includes a source of compressed oxygen and a source of a treatment liquid which can be selectively coupled to the dental unit to enable the apparatus to be used in a wide variety of dental treatments in the dental office.

OBJECTS AND BRIEF SUMMARY OF THE INVENTION

An object of the present invention is to provide novel dental apparatus which may be operated not only by a dentist or technician in a dental office to provide a patient with a wide variety of dental or oral treatments, but also by a user himself or herself in the user's home.

According to the present invention, there is provided dental apparatus which includes: a handpiece graspable at one end by a user, and a head at the opposite end of the handpiece including nozzle means for discharging a fluid. The apparatus further includes a first conduit connectible at one end to a source of a flowable material and connected at its opposite end to the nozzle means in the handpiece, a second conduit connectible at one end to a source of a gas (alone, or also to a source of a cleaning powder) and connected at its opposite end to the nozzle means in the handpiece. An electrical oscillating drive within the handpiece oscillates the head. A manual fluid selector device manually selects either the flowable material, the gas (and/or powder), or both, for conduction via their respective conduits to and through the nozzle means in the handpiece.

The nozzle means may include a single nozzle in the handpiece such that the fluid is discharged as a single jet of liquid, gas (with or without a cleaning powder), or a mixture of both, as selected by the manual fluid selector. Alternatively, the nozzle means may comprise two separate nozzles, one for discharging a liquid jet along a predetermined path, and the other for discharging a gas jet (with or without a cleaning powder) to intersect the path of the liquid jet.

The manual fluid selector device enables the user to select the type of fluid jet to be discharged according to the particular application. For example, the user may select to discharge the flowable material, e.g., water, a treatment liquid (e.g., one containing a therapeutic or antibiotic agent), or a flowable cleaning powder. The user may also select to discharge only a gas, e.g., sterile oxygen or air, a cleaning powder with the gas, or a mixture of a liquid and a gas to produce a spray.

According to further features in the described preferred embodiment, the handpiece includes the manual fluid selector device and also a manual frequency selector for selecting the frequency of the electrical oscillating drive according to the particular treatment to be applied.

According to further features in the described preferred embodiment, the head includes a quickly-attachable coupling for quickly attaching and detaching the head with respect to the handpiece. The apparatus is preferably equipped with a plurality of interchangeable heads, e.g., one including only the nozzle (or nozzles), a second one including the nozzle (or nozzles) and bristles of a toothbrush, and a third one including the nozzle (or nozzles) and the holder for a wooden toothpick.

The described apparatus further includes a saliva ejector receivable in the user's mouth, a vacuum pump for drawing saliva from the user's mouth via the saliva ejector, and a drain for draining the saliva.

As will be described more particularly below, apparatus may be constructed in accordance with the foregoing features of the invention for operation by a dentist or technician in a dental office, but also for operation by the user himself or herself in the user's home, to perform a wide variety of dental or oral treatments. For example, the handpiece may be used for ejecting water, a treatment liquid, oxygen, a powder, or any combination of the foregoing, for thoroughly cleaning the teeth, the spaces between the teeth, and the spaces between the teeth and gums. The oxygen can be used for creating an aerobic environment in the mouth for killing aerobic bacteria and also for accelerating wound healing. The treatment liquid can be a fluoride to increase the resistance of the teeth to decay, a therapeutic agent, a sensitivity-reducing agent such as amine fluoride, an anti-calculus agent, an antibiotic, etc. The powder could be an abrasive material for cleaning the teeth, implants, porcelain crowns and bridges, a therapeutic agent, an antibiotic, etc.

Further features and advantages of the invention will be apparent from the description below.

BRIEF DESCRIPTION OF THE DRAWINGS

The invention is herein described, by way of example only, with reference to the accompanying drawings, wherein:

and FIG. 6 illustrates another type of saliva ejector which may be used in the apparatus of FIG. 1.

DESCRIPTION OF A PREFERRED EMBDODIMENT

Figure 1:
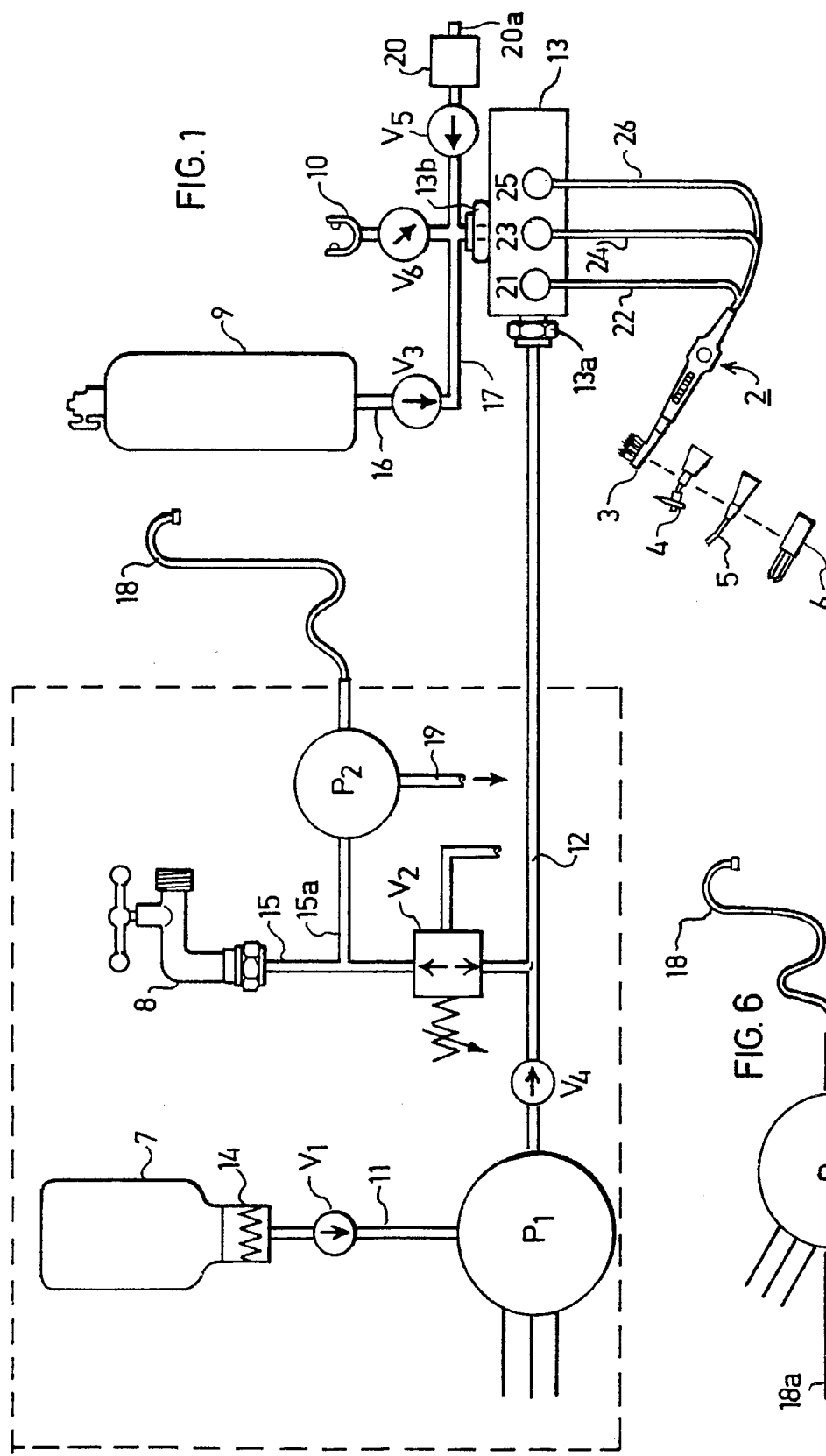
FIG. 1 illustrates one form of apparatus constructed in accordance with the present invention.

As indicated earlier, the apparatus illustrated in the drawings may be constructed for use in a dental clinic to be operated by the dentist or a technician; alternatively, it could be constructed for use in the user's home to be operated by the user himself or herself.

The apparatus illustrated in FIG. 1 includes a handpiece, generally designated 2, graspable at one end by the user, and including a head 3 at the opposite end receivable in the user's mouth for performing a selected dental or oral treatment as will be described below. For this purpose, head 3 is constructed as an interchangeable unit to enable any one of a plurality of different heads, shown at 4, 5 and 6 in FIG. 1, to be attached to the handpiece 2 according to the particular treatment to be made. The construction of head 3 is more particularly illustrated in FIG. 2. The constructions of the other interchangeable heads 4, 5 and 6 are more particularly illustrated in FIGS. 3, 4 and 5, respectively.

Handpiece 2 may be selectively supplied with any of the following: (a) a flowable material, such as a treatment liquid, from a container 7; (b) water, such as from a tap 8; (c) sterile oxygen from a pressurized oxygen tank 9; or (d) sterile air from a pressurized air source (not shown) to which quick-attachable connector 10 is connected. The illustrated apparatus further includes a source of powder 20, e.g., a powder container having an air inlet 20a for supplying powder with the air or oxygen.

Container 7 for the flowable material, e.g., treatment liquid, is connected by a line 11 to a pump $P_1$ under the control of an electrically-operated one-way valve $V_1$ to pump the liquid via a one-way Valve $V_4$ to a line 12 connected to inlet 13a of a junction unit 13. When container 7 contains a treatment liquid, the liquid is preferably heated by electrical heater 14 before being pumped to the junction unit 13.

The water tap 8 is connected by a line 15 and an electrically-operated one-way valve $V_2$ to line 12. Valve $V_2$ preferably includes a pressure regulator to regulate the pressure of the water supplied via the tap to line 12.

Oxygen tank 9 is connected via a line 16 and an electrically-operated one-way valve $V_3$ to another line 17 connected to a second inlet 13b of the junction unit 13. The quick-attachable connector 10, attachable to a source of compressed air, is connected by a similar valve $V_6$ and line 17 to inlet 13b of the junction unit. Powder source 20 (e.g., a portable powder air polisher, such as the "Densply/ Cavitron Prophy-Jet 30" (Reg. TMs), is also connected to inlet 13b via valve $V_5$.

The apparatus illustrated in FIG. 1 further includes a saliva ejector 18 receivable in the user's mouth to draw saliva therefrom by means of a vacuum pump $P_2$ to a drain 19. Vacuum pump $P_2$ may be a venturi pump producing a vacuum by the flow of water from tap 8; for this purpose, it includes a line 15a connected to line 15 leading from the water tap 8. FIG. 6 illustrates a variation wherein the saliva ejector, therein designated 18, is connected by an electrically-driven vacuum pump $P_3$ to drain the saliva from the patient's mouth via a drain 18a.

It will thus be seen that the junction unit 13 includes a liquid inlet 13a connected to line 12 for selectively inletting into the junction unit a treatment liquid from container 7, or water from tap 8, under the control of valves of $V_1$ and $V_2$, respectively. Junction unit 13 also includes a gas inlet 13b connected to line 17 for inletting pressurized oxygen from tank 9 or pressurized air from tank 10 under the control of valves $V_3$ and $V_6$, respectively, either with or without powder from unit 20 under the control of valve $V_5$.

Junction unit 13 includes a liquid outlet 21 connected by line 22 to handpiece 2, and a gas outlet 23 connected by line 24 to the handpiece 2. Junction unit 13 further includes an electrical power supply for an electrical oscillating drive within handpiece 2, as will be described more particularly below, and therefore the junction unit also includes an electrical outlet 25 connected by electrical conductor 26 to the handpiece. The three connections 22, 24 and 26 to the handpiece 2 are preferably enclosed within a common sheath (not shown).

Figure 2:
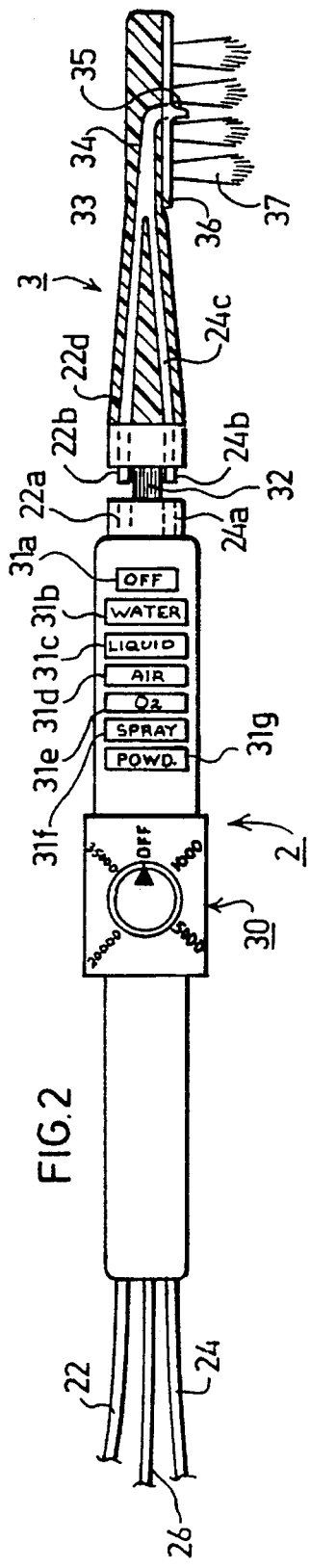
FIG. 2 is an enlarged view more particularly illustrating the handpiece in the apparatus of FIG. 1 with one type of head attached.

Handpiece 2, including its interchangeable head 3, is more particularly illustrated in FIG. 2. It includes a frequency selector 30 for selecting, via electrical conductor 26, the frequency of operation of the electrical oscillating drive circuit enclosed within the junction unit 13. The frequency selector is in the form of a knob which may be rotated to select any frequency up to 35 KHz.

Handpiece 2 further includes a fluid-flow selector constituted of six buttons 31a–31g. These buttons control the valves $V_1$–$V_5$ such that depressing button 31a closes all the valves so that no discharge is produced, depressing button 31b produces only a discharge of water, depressing button 31c produces only a discharge of the treatment liquid, depressing button 31d produces a discharge of air, depressing button 31e produces a discharge of oxygen, depressing button 31f produces a discharge of both air (or oxygen) and water (or treatment liquid), and depressing button 31g produces a discharge of powder in air (or oxygen).

The liquid line 22 extends through handpiece 2 and terminates in a coupling 22a at the end of the handpiece adapted to receive the replaceable head 3. Similarly, the gas line 24 extends through the handpiece and terminates in a coupling 24a.

The toothbrush head 3 is attached to the handpiece 2 by means of a magnetostrictive stack 32 carried by the head for oscillating it, and receivable within a socket of the handpiece. The magnetostrictive stack 32 is only partially shown in FIG. 2, but more fully shown in FIGS. 3, 4 and 5. Such constructions for attaching and oscillating the head of a dental implement at high frequencies are well known (e.g., as included in the above-mentioned "Dentsply/ Cavitron" Model 700-11), and therefore further details of construction and operation of the oscillating drive for the head are not set forth herein.

The interchangeable head 3 includes couplings 22b and 24b, cooperable with couplings 22a and 24a of handpiece 3, when the head is attached to the handpiece. These couplings are connected by conduits 22c, 24c extending through head 3 where they are connected at a juncture point 33 within the head to a common line 34 leading to a nozzle 35. Nozzle 35 projects through a brush holder 36 carrying a plurality of bristles 37.

Figure 3:
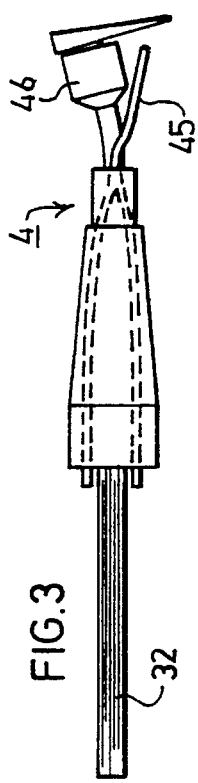
FIGS. 3 and 4 illustrate two further types of heads that may be used with the handpiece of FIG. 2.

FIG. 3 illustrates an interchangeable head, generally designated 4, which is of basically the same construction as described above with respect to the toothbrush head 3, except that instead of including a bristle holder (36, FIG. 2), head 4 includes a toothpick holder 46. The toothpick holder 46 may be of the same construction as described in U.S. Pat. No. 5,393,229. Otherwise the structure of head 4 is the same as described above with respect to FIG. 3, and therefore the same reference numerals have been used to identify corresponding parts in order to facilitate understanding.

Figure 5:
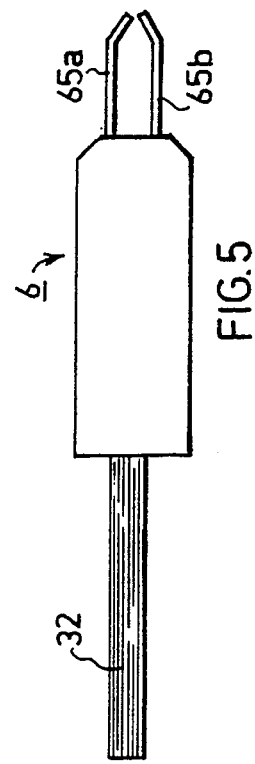
FIG. 5 illustrates a head similar to the type of FIG. 4 but including two nozzles for discharging separate jets of a liquid and a gas (with or without a powder)
Figure 4:
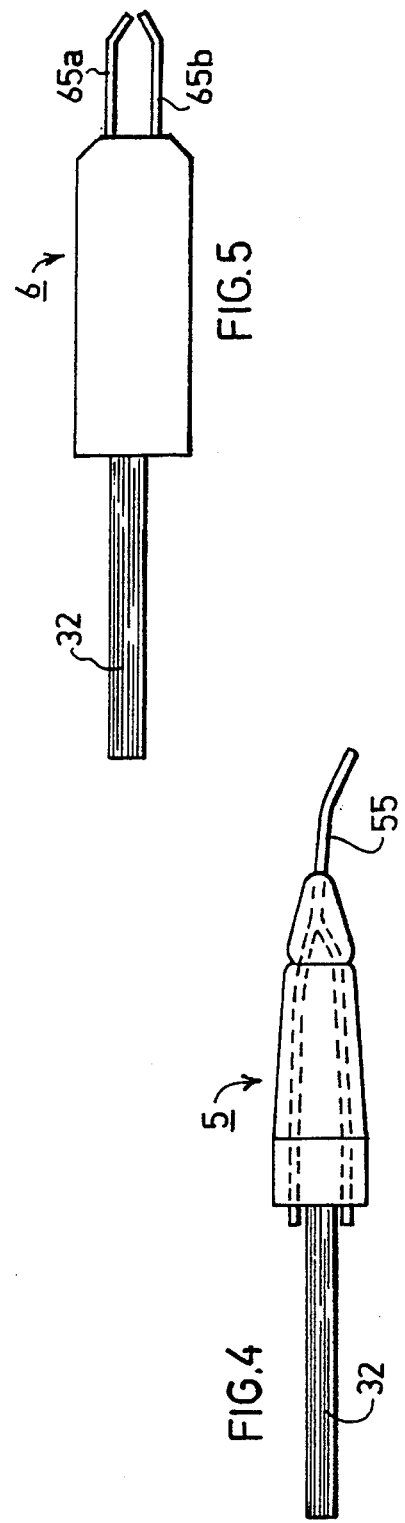

FIG. 5 illustrates the interchangeable head 5 which may also be of substantially the same construction as described above with respect to heads 3 and 4, except that interchangeable head 5 in FIG. 4 includes only the nozzle and does not include either the bristle holder (36) of the toothbrush head 3, nor the toothpick holder (46) of the toothpick head 4. Accordingly, head 5 of FIG. 4 includes only nozzle 55 for discharging the selected fluid.

In all the foregoing constructions, the interchangeable head includes a single nozzle (35, 45, 55) for discharging the selected fluid (liquid, gas, spray or powder). Interchangeable head 6 illustrated in FIG. 5, however, includes two nozzles 65a, 65b, respectively, one for discharging a liquid if selected, and the other for discharging a gas (with or without powder) if selected. The two nozzles are oriented so their paths intersect at the working area to receive the selected discharge. Thus, if both a liquid and a gas are selected to be discharged, each would issue from its respective nozzle 65a, 65b in the form of a jet with the two jets intersecting at the working area in the user's mouth. It has been found that such an arrangement, wherein the two jets issue separately and intersect at the working area, is very advantageous in many applications.

The manner of using the apparatus illustrated in the drawings will be apparent from the above description. Thus, if the toothbrush head 3 is to be used, it would be applied to the handpiece 2, and the user would then be able to select the type of discharge to be produced from its nozzle 35 by depressing the appropriate buttons 31a–31g, and would also be able to select the oscillating frequency by the frequency selector 30. If the toothpick head 4 is to be used, it may be quickly attached to the handpiece and similar selections may be made with respect to the material to be discharged and also the frequency of oscillations of the head. Either of the other two interchangeable heads 5, 6, may be attached and used in the same manner.

While the invention has been described with respect to one preferred embodiment, it will be appreciated that this is set forth merely for purposes of example, and that many variations may be made. For example, the interchangeable brush head 3, or toothpick holder head 4, could also include two nozzles, as shown in FIG. 6. Many other variations, modifications and applications of the invention may be made.

I claim:

1. Dental apparatus, comprising:

a handpiece graspable at one end by a user;

a head at the opposite end of the handpiece including nozzle means for discharging a fluid;

a first conduit connectible at one end to a source of a flowable material, and connected at its opposite end to said nozzle means in the handpiece;

a second conduit connectible at one end to a source of a gas, and connected at its opposite end to said nozzle means in the handpiece;

an electrical oscillating drive within said handpiece for oscillating said head;

and a manual fluid selector device for manually selecting either said flowable material, said gas, or both, for conduction via their respective conduits to and through said nozzle means in the handpiece.

2. The apparatus according to claim 1, wherein said nozzle means comprises a nozzle in said handpiece through which the fluid is discharged as a jet of liquid, gas, or a mixture of both, as selected by said manual fluid selector.

3. The apparatus according to claim 2, wherein said first and second conduits are connected together at a juncture within said handpiece.

4. The apparatus according to claim 1, wherein said nozzle means comprises two separate nozzles, one for discharging a liquid jet along a predetermined path, and the other for discharging a gas jet to intersect said path of the liquid jet.

5. The apparatus according to claim 1, wherein said handpiece includes said manual fluid selector device and also a manual frequency selector for selecting the frequency of said electrical oscillating drive.

6. The apparatus according to claim 1, wherein said head includes a quickly-attachable coupling for quickly attaching and detaching the head with respect to the handpiece.

7. The apparatus according to claim 1, wherein said head also includes bristles of a toothbrush in addition to said nozzle.

8. The apparatus according to claim 1, wherein said head also includes a holder for a wooden toothpick in addition to said nozzle.

9. The apparatus according to claim 1, wherein said apparatus includes a supply of a flowable material connected to said first conduit, and a valve controlled by said manual fluid selector device for controlling the flow of said flowable material via said first conduit to said nozzle means in the handpiece.

10. The apparatus according to claim 9, wherein said supply of flowable material is a liquid source.

11. The apparatus according to claim 10, wherein said liquid source is a water tap.

12. The apparatus according to claim 10, wherein said liquid source is a container containing a supply of a treatment solution.

13. The apparatus according to claim 10, wherein said liquid source is a pipe selectively connectible to a water tap or to a container containing a supply of a treatment solution.

14. The apparatus according to claim 1, wherein the apparatus further includes a supply of a gas connected to said second conduit in the handpiece, and a valve controlled by said manual fluid selector device in the handpiece for controlling the flow of gas to said second conduit in the handpiece.

15. The apparatus according to claim 14, further including a container containing a supply of a flowable powder and a valve controlled by said manual fluid selector device for controlling the flow of said powder with said gas to said second conduit in the handpiece.

16. The apparatus according to claim 14, wherein said supply of gas is a source of pressurized oxygen.

17. The apparatus according to claim 14, wherein said supply of a gas is a source of pressurized air.

18. The apparatus according to claim 1, wherein said apparatus further includes a saliva ejector receivable in the user's mouth, a vacuum pump for drawing saliva from the user's mouth via the saliva ejector, and a drain for draining the saliva.

19. The apparatus according to claim 18, wherein said vacuum pump is a venturi pump connected to a water tap.

20. The apparatus according to claim 18, wherein said vacuum pump is an eletrically-driven pump connected to an electrical power supply.

\* \* \* \* \*